United States Patent [19]
Kilger et al.

[11] Patent Number: 6,107,032
[45] Date of Patent: Aug. 22, 2000

[54] METHOD FOR THE DIRECT, EXPONENTIAL AMPLIFICATION AND SEQUENCING OF DNA MOLECULES AND ITS APPLICATION

[75] Inventors: Christian Kilger; Svante Pääbo, both of München, Germany

[73] Assignee: Roche Diagnostics GmbH, Mannheim, Germany

[21] Appl. No.: 08/991,347

[22] Filed: Dec. 16, 1997

[30] Foreign Application Priority Data

Dec. 20, 1996 [EP] European Pat. Off. ............ 196 53 439

[51] Int. Cl.$^7$ .............................. C12Q 1/68; C12P 19/34; C07H 21/04
[52] U.S. Cl. ........................... 435/6; 435/91.2; 536/24.33
[58] Field of Search ..................... 435/6, 91.2; 536/24.33

[56] References Cited

U.S. PATENT DOCUMENTS

| | | | |
|---|---|---|---|
| 4,683,202 | 7/1987 | Mullis | 435/91 |
| 4,962,020 | 10/1990 | Tabor et al. | 435/6 |
| 5,338,671 | 8/1994 | Scalice et al. | 435/6 |
| 5,409,811 | 4/1995 | Tabor et al. | 435/6 |
| 5,427,911 | 6/1995 | Ruano | 435/6 |
| 5,512,462 | 4/1996 | Cheng | 435/91.2 |
| 5,556,772 | 9/1996 | Sorge et al. | 435/91.2 |
| 5,587,287 | 12/1996 | Scalice et al. | 435/6 |
| 5,693,517 | 12/1997 | Gelfand et al. | 435/193 |
| 5,789,168 | 8/1998 | Leushner et al. | 435/6 |
| 5,830,657 | 11/1998 | Leushner et al. | 435/6 |

FOREIGN PATENT DOCUMENTS

| | | |
|---|---|---|
| 0 727 496 | 8/1996 | European Pat. Off. . |
| WO 94/05797 | 3/1994 | WIPO . |

OTHER PUBLICATIONS

International Publication No. WO 96/41014 published Dec. 19, 1996.
International Publicaiton No. WO 96/10640 published Apr. 11, 1996.
International Publication No. WO 94/26766 published Nov. 24, 1994.
Chemical Abstracts, vol. 125, No. 25, 1996, p. 393, 125:319052.
Tabor et al., Proc. Natl. Acad. Sci. USA, vol. 92, pp 6339–6343, Jul. 1995, "A single residue in DNA polymerases of the *Escherichia coli* DNA polymerase I family is critical for distinguishing between deoxy–and dideoxyribonucleotides".
Kilger et al., Nucleic Acids Research, vol. 25, No. 10, May 1997, pp. 2032–2034 "Direct DNA sequence determination from total genomic DNA".
International Publication No. WO 93/02212, published Feb. 4, 1993.
Hwang et al., Analytical Biochemistry, vol. 231, No. 2, Nov. 1995, pp. 460–463, "Direct automated sequencing of singl lambda–phage plaques by exponential amplification sequencing".
Sarkar et al., Nucleic Acids Research, 1995, vol. 23, No. 7, pp. 1269–1270, "Semi Exponential cycle sequencing".
Kilger et al., Biol. Chem., vol. 378, pp 99–105, Feb. 1997, "Direct exponential Amplification and Sequencing (DEXAS) of Genomic DNA".
International Publication No. WO 97/42348, published Nov. 13, 1997.
International Publication No. WO 97/40939, published Nov. 6, 1997.
International Publication No. WO 97/23650, published Jul. 3, 1997.
International Publication No. WO 97/41257, published Nov. 6, 1997.
International Publication No. WO 97/41258, published Nov. 6, 1997.
International Publication No. WO 97/41259, published Nov. 6, 1997.
Deng et al., Journal of Microbilogical Methods, vol. 17 (1993) 103–113, "Simultaneous amplification and sequencing of genomic DNA (SAS) . . . ".
Rao, Analytical Biochemistry, vol. 216, 1–14 (1994), "Direct Sequencing of Polymerase Chain Reaction–Amplified DNA".
Chemical Abstracts, vol. 125, 1996, Ref. 319052 v.

*Primary Examiner*—Bradley Sisson
*Assistant Examiner*—Jeffrey Siew
*Attorney, Agent, or Firm*—Nikaido Marmelstein Murray & Oram LLP

[57] ABSTRACT

A method is described for the direct, exponential amplification and sequencing ("DEXAS") of a DNA molecule from a complex mixture of nucleic acids, wherein truncated DNA molecules as well as DNA molecules of full length are synthesized simultaneously and exponentially between two positions on the said DNA molecule, which initially contains a DNA molecule in a thermocycling reaction, a first primer, a second primer, a reaction buffer, a thermostable DNA polymerase, a thermostable pyrophosphatase (optionally), deoxynucleotides or derivatives thereof and a dideoxynucleotide or derivatives thereof.

42 Claims, 8 Drawing Sheets

Fig. 6A

```
ambiguities
Cy5         CNNCGAGTCG ACGTATCGA TAACTTGATA TCGAATTCCT GCAGCCGGKK GGATCCGCCC    60
FITC
ambiguities
Cy5         TACACCAGTC TTGTAAACCG GAAACAGAAA CTTTCTCCCC AGGGCAACTC AGAAAGAAAG   120
FITC
ambiguities
Cy5         TACTCAACTT CACCACCAAC ATCCAAAACT GGCATTCTAA TTTAAACTAC TTTCTGCATT   180
FITC
ambiguities                                                                    240
Cy5         CTATGGGGGT GCAAGCTTTA AGTGCAACTT AAGTACTAAT TTATTTATCA GACCCTTATG    33
FITC                                                   CTT AAGTACTAAT TTATTTATCA GACCCTTATG
                                                                       YY K
ambiguities
Cy5         TAATTTGTGC ATTACTGCTA GCCAACATGA ATGTTATATA GTACTCATAA ATGCYTAACT   300
FITC        TAATTTGTGC ATTACTGCTA GCCAACATGA ATGTTATATA GTACTCATAA ATGYTTKACT    93
                         T
ambiguities
Cy5         GTACATAGCA CATATTTTWA CATACATACT ACATATTCTC AAGA-ACATG CTTACAAGCA   360
FITC        GTACATAGCA CATATTTTTA CATACATACT ACATATTCTC AAGARACATG CTTACAAGCA   153
                                                              R
ambiguities
Cy5         AGAACCCCAA TGAACCAACC AACTGTAGAA CATAACATCA ACTTCAAAGA CCAAGCACAT   420
FITC        AGAACCCCAA TGAACCAACC AACTGTAGAA CATAACATCA ACTTCAAAGA CCAAGCACAT   213
                                                              R
ambiguities
Cy5         CCCCMAGAAT ATCAACTAAC TTAACTTTTT ATTCATCATA CATAGCACAT TAAACGGTTC   480
              M
```

```
FITC         CCCCCAGAAT ATCAACTAAC TTAACTTTTT ATTCATCATA CATRGCACAT TAAACGGTTC    273
ambiguities
Cy5          ATCGGACATA GCACATTTCA GTCAAACAAA TTCCTATCAC CACGGATACC CCCCTCAGTT    540
FITC         ATCGGACATA GCACATTTCA GTCAAACAAA TTCCTATCAC CACGGATACC CCCCTCAGTT    333
ambiguities                KK
Cy5          AGGTGTCCCT TATTCACCAT CCTCCGTGAA ATCAATATCC CGCACAAGAG TGCTACTCTC    600
FITC         AGGTGTKKCT TATTCACCAT CCTCCGTGAA ATCAATATCC CGCACAAGAG TGCTACTCTC    393
ambiguities
Cy5          CTCGCTCCGG GGGGCTAGAG CGGCCGCCAC CGCGGTGGAG CTCCMGCTTT TGTNCCCTTT    660
FITC         CTCGCTCCGG GGGG                                                       407
ambiguities
Cy5          ATGAGGCTC                                                             668
```

Fig. 6B

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:PRIMER

<400> SEQUENCE: 1
gattctaatt taaactattc tctgttc                                27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:PRIMER

<400> SEQUENCE: 2
ttatgaccct gaagtaggaa ccagatg                                27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:PRIMER

<400> SEQUENCE: 3
ggaggcactt gccaccctgc acactgg                                27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:PRIMER

<400> SEQUENCE: 4
ctcctccacc gcttcttgtt ctgcttg                                27

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:PRIMER

<400> SEQUENCE: 5
ggctggtcct gccgctgctt gtcat                                  25

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:PRIMER

<400> SEQUENCE: 6
ctgctcccca gtggatcggg tgtaaac                                27

METHOD FOR THE DIRECT, EXPONENTIAL AMPLIFICATION AND SEQUENCING OF DNA MOLECULES AND ITS APPLICATION

The present invention relates to a method for the direct, exponential amplification and sequencing of DNA molecules as well as the use of the method. The direct, exponential amplification and sequencing of DNA molecules is referred to as "DEXAS" in the following.

TECHNICAL FUNDAMENTALS

DNA sequence determination as developed by Sanger et al. ((1977) Proc. Natl. Acad. Sci. USA 74, 5463–5467) is usually carried out with a T7 DNA polymerase (Tabor S. and Richardson, C. C. (1989) Proc. Natl. Acad. Sci. USA 86, 4076–4080). This method requires relatively large amounts of a purified, single-stranded DNA template. Recently cycle sequencing has been developed (Murray, V. (1989) Nucleic Acids Res. 17, 8889). This method does not require a single-stranded template and allows the sequence reaction to be initiated with relatively small amounts of template. However, the template DNA has to be purified to almost complete homogeneity and is usually prepared by means of cloning in plasmids (Bolivar, F. et al., (1977) Gene 2, 95–113) and subsequent plasmid purification (Birnboim, H. C. and Doly, J. (1979) Nucleic Acids Res. 7, 1513–1523) or by means of PCR amplification (Mullis, K. B. and Faloona, F. A. (1987) Methods Enzymol. 155, 335–350). Only one primer is used in both of the methods described above.

In one embodiment of the cycle sequencing which is referred to as "coupled amplification and sequencing" or "CAS" Ruano and Kidd ((1991) Proc. Natl. Acad. Sci. USA 88, 2815–2819; U.S. Pat. No. 5,427,911) have shown that one can use a two-step protocol to generate sequences from DNA templates. In the first step 15 PCR cycles are carried out with Taq DNA polymerase in the absence of dideoxynucleotides in order to prepare an adequate amount of sequencing template. In a second step in which dideoxynucleotides and a labelled primer are added, CAS produces the sequence as well as the additional amplification of the target sequence. Two primers are used in both steps of the method.

Taq DNA polymerase, that is used in coupled DNA sequencing reactions strongly discriminates against ddNTPs and preferably incorporates dNTPs if it is furnished with a mixture of ddNTPs as well as dNTPs. In addition it incorporates each ddNTP, i.e. ddATP, ddCTP, ddGTP, ddTTP, with a strongly varying efficiency. Hence the optimization of the CAS process requires careful titration of the dideoxynucleotides.

Furthermore since coupled amplification and sequencing depends on the amount of the initial DNA, the distance between the two primers and the concentrations and the ratios of the ddNTPs and dNTPs relative to one another and to each other, the optimization of coupled amplification and sequencing reactions (CAS) requires that the reaction conditions are individually optimized for a particular DNA fragment.

All the methods described above require an interruption between the first step of exponential amplification of the template DNA and the second step for the synthesis of truncated DNA molecules and also require the individual optimization of a given DNA fragment which can be tedious and time-consuming and can lead to errors especially when sequencing a large number of different DNA molecules or when processing large amounts of samples in a hospital or laboratory or when sequencing rare samples for forensic or archaeological studies.

For this reason it would be advantageous to have available a method for sequencing nucleic acids which simultaneously potentiates the exponential amplification of molecules of full length and of molecules of truncated length in the reaction which leads to a reduction of the required amount of starting nucleic acid molecules and does not require an interruption of the exponential amplification step and of the sequencing step so that the whole reaction can be carried out more rapidly and with fewer manipulations.

SUMMARY OF THE INVENTION

The object of the present invention is to provide an improved, rapid and reliable method for sequencing DNA molecules, preferably genomic DNA.

A further object of the present invention is to provide a direct method for nucleic acid sequencing which simultaneously increases the exponential amplification of molecules of full length as well as of molecules of truncated length in the reaction which leads to a reduction of the initial amount of nucleic acid molecules that are required for the cycling reaction.

A further object of the present invention is to provide an improved, rapid and reliable method for sequencing DNA molecules, preferably genomic DNA that can be carried out in a single step in a single container.

A further object of the present invention is to provide an application according to the invention for sequence determination in medical diagnostics, forensics and population genetics.

Further objects of the invention are obvious to a person skilled in the art from the description.

In contrast to the above-described "CAS" method a DNA polymerase is used as the thermostable DNA polymerase which, compared to wild-type Taq DNA polymerase, has a reduced discrimination against the four ddNTPs in the buffer and under the conditions that are used for the thermocycling. More preferably a DNA polymerase is used which carries a "Tabor-Richardson" mutation or a functional derivative thereof which also has no 5'-3' exonuclease activity such as e.g. AmplitaqFS™ (Taq DNA polymerase (-exo5'-3') (F667Y), Tabor and Richardson (1995), loc. cit.), Taquenase™ (Taq DNA polymerase Δ235 (-exo5'-3') (F667Y), Tabor and Richardson (1995), loc. cit.) and Thermo Sequenase™ (Taq DNA polymerase (-exo5'-3') (F667Y), Tabor and Richardson (1995), loc. cit.) as well as mixtures thereof or other DNA polymerases and mixtures thereof which are thermostable can also be used in the method of the present invention.

Surprisingly the use of a DNA polymerase which, in comparison to wild-type Taq DNA polymerase, has a reduced discrimination against the four ddNTPs, enables the simultaneous and exponential synthesis of truncated as well as of full fragments from the start of the cycling reaction. Hence the present invention concerns a method for the direct sequencing of a nucleic acid molecule from a complex mixture of nucleic acids, such as e.g. total genomic human DNA, containing a reaction buffer, deoxynucleotides or derivatives thereof and a dideoxynucleotide or another terminating nucleotide and a thermostable polymerase which has a reduced discrimination against ddNTPs in comparison to wild-type Taq DNA polymerase. Within the sense of the present invention direct sequencing means that the nucleic acid fragment to be sequenced is simultaneously amplified and sequenced in one step without interrupting the reaction and without prior amplification of the nucleic acid fragment to be sequenced by the known methods and in such a manner that an unequivocal sequence ladder is readable.

The principle of DEXAS is that the initial and subsequent cycle sequencing reaction is carried out with two primers, a first primer, and a second primer which lies on the strand complementary to the first, which are preferably present in a non-equimolar ratio and serve to simultaneously produce adequate template molecules of fill length as well as truncated molecules which contribute to the sequencing of the DNA molecule. Four reactions are prepared, one for the determination of each base, so that each reaction contains two primers preferably in a non-equimolar ratio to one another of which either one is labelled and the other is unlabelled or both are differently labelled. The said non-equimolar ratio between the first primer and the second primer enables the simultaneous and exponential synthesis of the truncated as well as of the full fragments from the start of the cycling reaction. Furthermore each reaction contains from the start the DNA template to be sequenced as well as a buffer solution, thermostable DNA polymerase, thermostable pyrophosphatase (optionally), the four deoxynucleotides or derivatives thereof and a dideoxynucleotide or a terminating nucleotide e.g. 3-aminonucleotide or 3'-ester-derivatized nucleotides.

Thereafter cycles for denaturing and extension are carried out so that in each of these cycles two types of extension products are formed from each primer. Each primer functions such that it initiates extension products which are long enough to reach the other primer position. Simultaneously products are initiated by each primer which, due to the incorporation of a dideoxynucleotide, are terminated before the other primer position is reached. The former said products (products of full length) serve in the following cycles as a template for the production of further DNA strands of full length and are also used as templates for extensions that contribute to the sequence reaction, and the latter products (truncated products) accumulate during the cycles and contribute to the sequence ladder that is generated. Hence DEXAS results in the simultaneous exponential production of a sequencing template and a sequence ladder in a single tube without having to interrupt the thermocycling reaction.

Therefore the use of the present invention enables the DNA sequence of multicopy and single-copy regions of DNA to be determined in a single step.

Hence the present invention for the first time provides a method which enables the nucleic acid to be sequenced to be simultaneously amplified and sequenced from a complex mixture of nucleic acids, such as e.g. total genomic human DNA, without prior amplification by the known methods, in one step i.e. without interrupting the reaction and such that an unequivocal sequence ladder is readable wherein at least one thermostable DNA polymerase, a nucleic acid molecule, a first primer, a second primer, a reaction buffer, deoxynucleotides or derivatives thereof and at least one dideoxynucleotide or another terminating nucleotide is present in the initial reaction mixture.

Furthermore the aforementioned object and goals of the present invention are achieved by the provision of a method for sequencing DNA molecules in which truncated DNA molecules as well as DNA molecules of full length are simultaneously and exponentially synthesized between two positions on the said DNA molecule in a thermocycling reaction which initially contains a DNA molecule, a first primer, a second primer, a reaction buffer, a thermostable DNA polymerase, thermostable pyrophosphatase (optionally), deoxynucleotides or derivatives thereof, and a dideoxynucleotide or another terminating nucleotide thereof wherein the initial ratio of the said primers in the said thermocycling reaction is not equal to 1.

In a preferred embodiment of the method of the invention the ratio of the said primers to one another is about 2:1 to about 3:1, most preferably 2:1.

In a further preferred embodiment of the method of the invention the said primers have such a length that the signal-to-noise ratio between the specific truncated DNA molecules and the unspecific DNA molecules is large enough not to substantially prevent the reading of the sequence. The said primers preferably have a length of at least 25 nucleotides.

Primers can be synthesized by means of methods known in the state of the art. For example primers can be synthesized using known methods which do not significantly change the stability or function of the said primers during the nucleic acid sequencing method of the present invention.

Furthermore the PNA-DNA hybrid oligonucleotides (see Finn, P. J. et al., N.A.R. 24, 3357–3363 (1996), Koch, T. et al., Tetrahedron Letters, 36, 6933–6936 (1995), Stetsenko, D. A, et al., Tetrahedron Letters 37, 3571–3574 (1996), Bergmann, F. et al., Tetrahedron Letters 36, 6823–6826 (1995) and Will, D. W. et al., Tetrahedron 51, 12069–12082 (1995)) are also regarded as primers for the method according to the invention.

In a further preferred embodiment of the invention the said first primer is labelled. Moreover it is preferable that the said first primer and second primer are labelled differently. Any suitable agents or methods known in the state of the art can be used as single or differential labelling agents and methods, provided that they do not significantly change the stability or function of the said primer in the DNA sequencing method of the present invention. For example single and differential labels can be selected from the group which comprises those enzymes such as β-galactosidase, alkaline phosphatase and peroxidase, enzyme substrates, coenzymes, dyes, chromophores, fluorescent, chemiluminescent and bioluminescent labels such as FITC, Cy5, Cy5.5, Cy7, Texas-red and IRD40 (Chen et al., (1993), J. Chromatog. A 652: 355–360 and Kambara et al. (1992), Electrophoresis 13: 542–546) ligands or haptens such as e.g. biotin and radioactive isotopes such as $^3$H, $^{35}$S, $^{32}$P, $^{125}$I and $^{14}$C.

The method according to the invention can also be carried out as a "hot start" method. In this case it is ensured that the activity of the polymerase or polymerases only starts at an increased temperature in order to suppress a polymerization on unspecifically hybridized primers at lower temperatures. One possibility is that the thermocycling reaction additionally contains a polymerase-inhibiting agent. Polymerase antibodies are for example available commercially which only denature at higher temperatures and thus release enzyme activity of the polymerase. However, polymerases modified by genetic engineering that are present in an inactive form at lower temperatures would also be conceivable.

DEXAS is relatively insensitive to various buffers and various deoxynucleotides and dideoxynucleotide concentrations and can be carried out using various thermostable DNA polymerases.

The number of thermocycles can be from about 18 to about 50 cycles depending on the amount of template DNA and its purity.

Buffer components which can be used can include Tris-HCl at a pH of about 9.0 to 9.5 and at a concentration of about 10 to 30 mM, ammonium sulfate at a concentration of about 10 to 20 mM preferably 15 mM, $MgCl_2$ at a concentration of about 3.5 to 5.5 mM optionally about 0.05 mM mercaptoethanol, about 0.28% Tween20® and/or about 0.02% Nonidet 40® but, however, are not limited to these.

Deoxynucleotides may be selected from dGTP, dATP, dTTP and dCTP but are not limited to these. According to the invention it is additionally also possible to use derivatives of deoxynucleotides which are defined as those deoxynucleotides which are able to be incorporated by a thermostable DNA polymerase into growing DNA molecules that are synthesized in the thermocycling reaction. Such derivatives can include thionucleotides, 7-deaza-2'-dGTP, 7-deaza-2'-dATP as well as deoxyinosine triphosphate that can also be used as a substitute deoxynucleotide for dATP, dGTP, dTTP or dCTP, but are not limited to these. The aforementioned deoxynucleotides and derivatives thereof are preferably used at a concentration between about 300 $\mu$M and 2 mM.

Dideoxynucleotides can be selected from ddGTP, ddATP, ddTTP and ddCTP but, however, are not limited to these. According to the invention it is also additionally possible to use derivatives of dideoxynucleotides which are defined as those dideoxynucleotides that are able to be incorporated by a thermostable DNA polymerase into growing DNA molecules that are synthesized in a thermo-cycling reaction. In addition it is also possible to use other terminating nucleotides e.g. 3'-amino nucleotide or 3'-ester-derivatized nucleotides. Preferred concentrations of ddNTPs are between about 1 and 5 $\mu$M.

In the method according to the invention the preferred ratio of dNTPs to ddNTPs (dNTPs:ddNTPs) is between 100:1 and 1000:1 preferably between 300:1 and 600:1.

In a further preferred embodiment of the method of the invention the said method is carried out at a temperature at which the signal-to-noise ratio between the specific truncated DNA molecules and the unspecific DNA molecules is large enough not to substantially impede reading of the sequence. It is less important to optimize the annealing temperature. In the case of human single-copy DNA sequences the highest possible annealing temperature drastically reduces the background. In this case the annealing and synthesis steps of the thermocycling reaction are preferably carried out at a minimum temperature of 62° C., more preferably at 66° C. and most preferably at at least about 68° C.

The template of the DNA molecule to be sequenced is preferably present as a total genomic DNA molecule which does not have to be cloned or purified, but this may be the case. In one embodiment of the invention the genomic DNA has a length of more than or equal to 2 kb. Other forms of DNA that can be used as templates include cloned or uncloned mitochondrial DNA, partially purified or unpurified DNA such as e.g. plasmid DNA of bacterial colonies. DEXAS functions well with about 250 ng template DNA for the determination of mitochondrial DNA sequences and about 1 $\mu$g template DNA for determining single-copy DNA sequences such as e.g. total genomic DNA, but it also functions with smaller amounts of mitochondrial or genomic DNA. The method according to the invention can also be used for the direct sequencing of unpurified single-stranded or double-stranded DNA from bacteriophages. DEXAS is in addition relatively independent of the base composition of the template.

In a preferred embodiment the method according to the invention is furthermore characterized in that each thermocycling reaction to determine the position of A, G, C and T in the said DNA molecule is carried out in a single step, in a single container, vessel or tube.

Suitable sources of nucleic acid molecules in the method according to the invention are body fluids such as sperm, urine, blood or fractions of these, hairs, an individual cell, cells or fractions thereof, hard tissue such as bones or soft tissue or fractions thereof and cell cultures or fractions thereof.

The present invention also serves for the application of the method according to the invention for the determination of a nucleotide sequence of a given nucleic acid molecule e.g. for sequencing Shotgun libraries with two labels for large-scale genome projects and in medical diagnostics, forensics and population genetics. The method of the present invention can be used to detect genetic mutations or polymorphisms, to identify the origin of the sequenced nucleic acid or to detect the presence of foreign or infectious agents in a sample.

The present invention relates to all combinations of all procedures of the above methods.

After preparation the sequencing reactions can be loaded directly onto a sequencing gel such as e.g. after addition of a commonly used application buffer (e.g. formamide which contains 20 mM EDTA (pH 7.4) and 6 mg/ml dextran blue) and denaturation (e.g. for 4 minutes at 96° C.). The sequence ladder can be read according to known methods. The method of the invention is well suited for automation. Since the two primers in the reaction are provided with different labels which can for example be detected with two different wavelengths, the method of the present invention enables the simultaneous sequencing of both strands of a template and the detection of both reactions in one or several gel lanes. In general many DEXAS reactions that are carried out using different dyes can be carried out simultaneously in the same tube and applied to a sequencing instrument that is equipped with several lasers or be detected by other methods such as e.g. autoradiography.

A further subject matter of the present invention is a kit for the direct sequencing of a nucleic acid molecule from a complex mixture of nucleic acids, such as e.g. total genomic human DNA, containing a reaction buffer, deoxynucleotides or derivatives thereof and a dideoxynucleotide or a further terminating nucleotide and a thermostable polymerase which has a reduced discrimination against ddNTPs compared to wild-type Taq DNA polymerase. Within the sense of the present invention direct sequencing means that the nucleic acid fragment to be sequenced is simultaneously amplified and sequenced, without prior amplification of the nucleic acid fragment to be sequenced by the known methods, in a single step without interrupting the reaction and such that an unequivocal sequence ladder can be read.

A further subject matter of the present invention is a kit for the direct sequencing of a nucleic acid molecule of a complex mixture of nucleic acids containing a reaction buffer, deoxynucleotides or derivatives thereof and a dideoxynucleotide or another terminating nucleotide, a thermostable polymerase and two primers whose ratio is larger than 1. The kit particularly preferably contains a thermostable polymerase which has a reduced discrimination against ddNTPs in comparison to the d-type Taq DNA polymerase.

BRIEF DESCRIPTION OF THE FIGURES

FIG. 3A shows a sequence of the human p53 gene whereas FIG. 3B shows a sequence of the human CCR-5 gene (see text for details). The sequence was processed with the A.L.F. software and was not edited manually. A total of 305 bases was determined in the case of the p53 gene whereas 343 bases were determined for the CCR-5 gene.

FIGS. 6A and 6B. The insert of a plasmid was sequenced from both sides in a reaction using a FITC-labelled 'T3' primer and an opposite Cy5-labelled 'universal' primer. The simultaneous use of two differently labelled oligonucleotides in a DEXAS reaction allowed the 548 base insert to be sequenced without leaving ambiguous positions. The primers were positioned at a distance of 670 bp to one another.

DETAILED DESCRIPTION OF THE INVENTION

Figure 1:
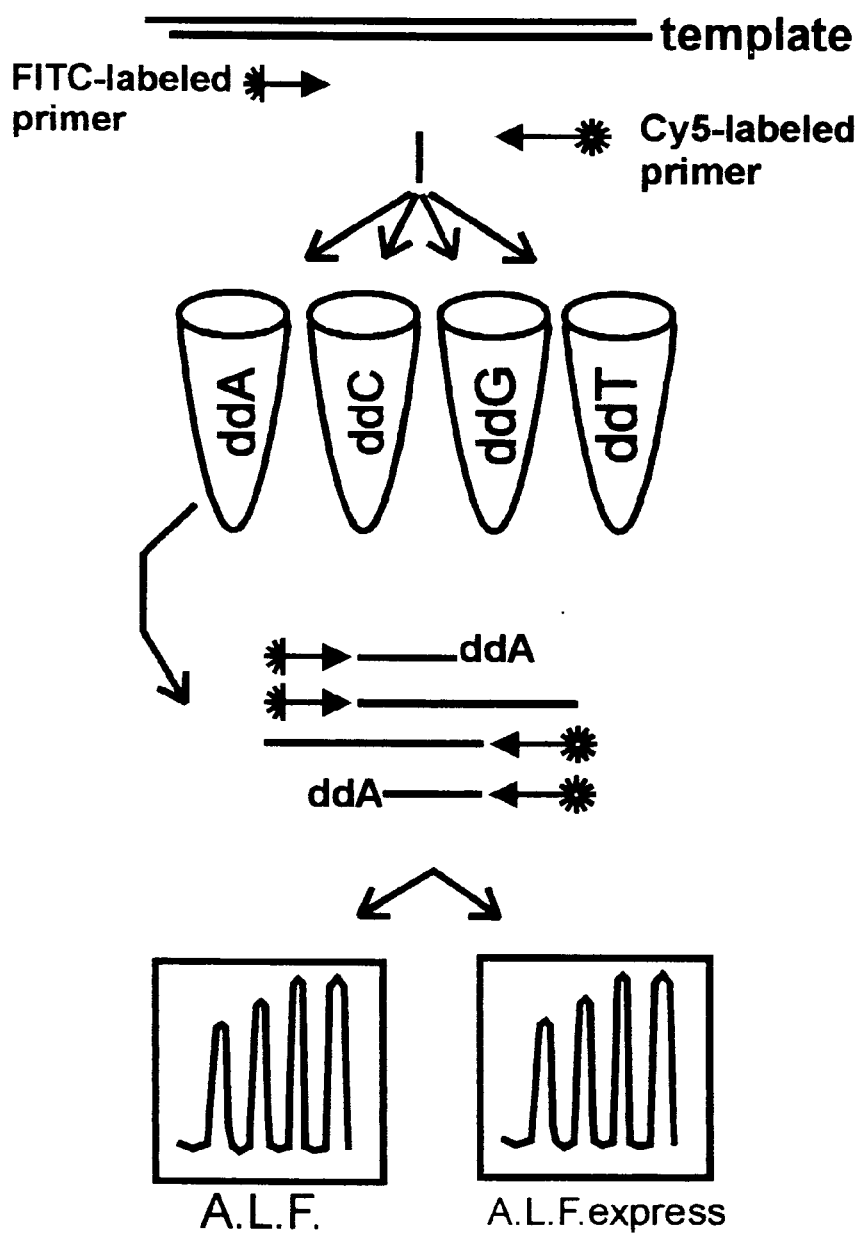
FIG. 1 Schematic representation of DEXAS. Two oligonucleotides (27 mers), either a labelled and an unlabelled oligonucleotide or an oligonucleotide labelled with FITC and an oligonucleotide labelled with Cy5 (ratio 2:1) are mixed in four tubes with human genomic DNA (250 ng to 3 µg), a heat-resistant DNA polymerase, the four deoxynucleotides and in each case one of the dideoxynucleotides. Cycles for denaturing and subsequent annealing and extension are carried out. During each extension the primers are either extended up to the complementary primer position or they are interrupted by the incorporation of a dideoxynucleotide. In subsequent cycles these former products serve as templates for the further generation of products of full length as well as for the termination reactions whereas the latter products accumulate during all of the cycles that are carried out and contribute to the sequence signal. After the cycling the reactions are denatured and, depending on their label, are either analysed on an A.L.F. or an A.L.F. express.
Figure 2:
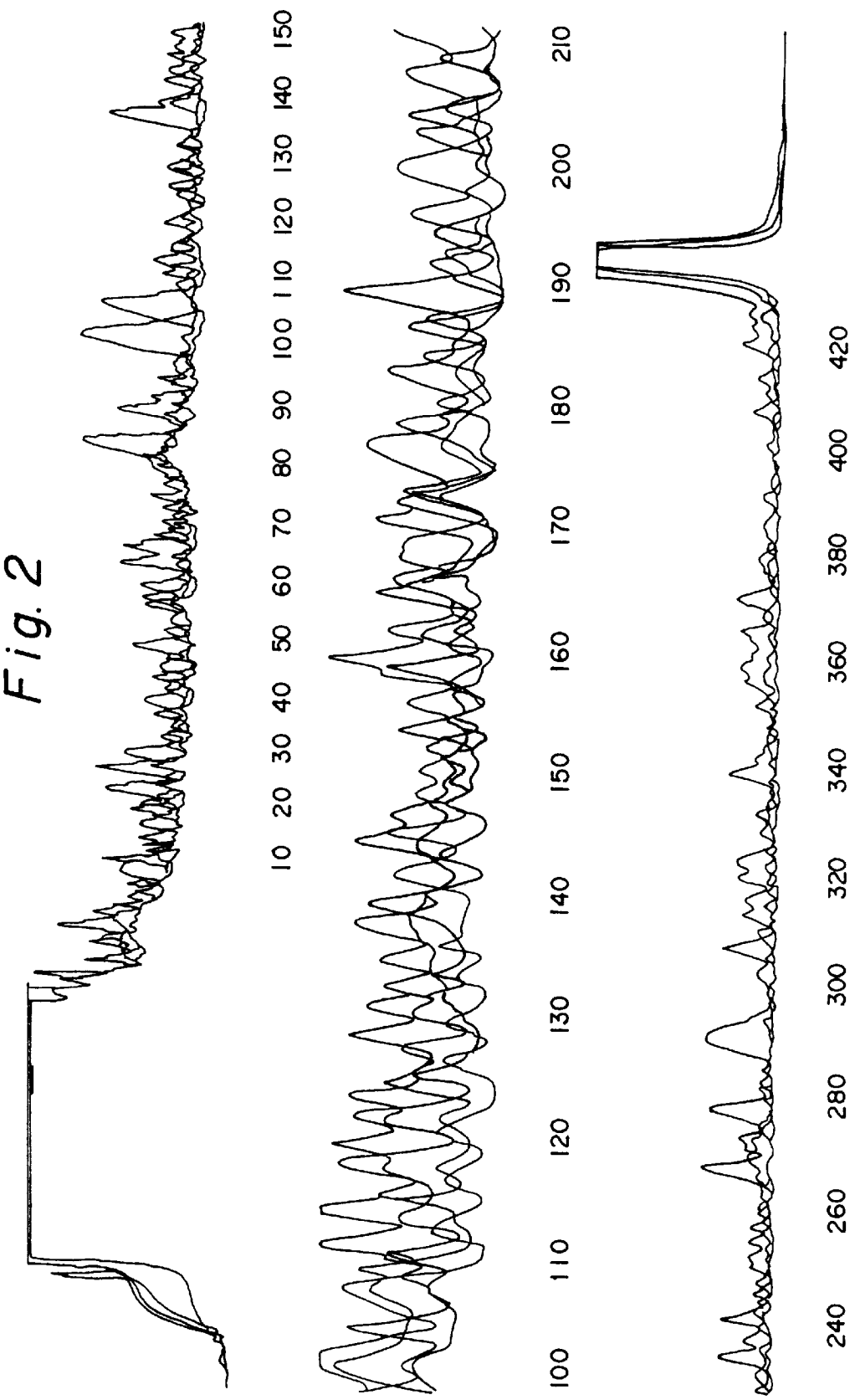
FIG. 2. DEXAS reaction carried out on a 521 bp segment of the human mitochondrial control region. Eight pmol of an FITC-labelled (mtDNA1-L16026) and 4 pmol of an unlabelled primer (mtDNA2-H16498) were used together with 250 ng of total genomic human DNA (see text for details). A strong signal can be seen before the first processed base and a strong stop can be seen at about base number 440. The sequence was processed with the A.L.F. software and was not edited manually. A total of 433 bases was determined. A sequence was obtained from the sequence traces shown in FIG. 2, though the sequence is not shown in FIG. 2.

The invention is described in more detail by the following non-limiting examples.

EXAMPLE 1

Template Preparation

Total genomic human DNA was prepared from 2 ml blood samples using a rapid cleaning kit (Cambridge Molecular Technologies Ltd., Cambridge, UK). Purified DNA was diluted in ddH$_2$O to a concentration of 175 ng per µl.

Sequencing Reagents and Conditions

Unlabelled and FITC-labelled oligonucleotides were synthesized with an ABI DNA/RNA synthesizer model 392. Cy5-labelled oligonucleotides were obtained from the Pharmacia Biotech Company (Freiburg, Germany). The following oligonucleotides were used in each case to sequence the mitochondrial control region (mtDNA), the p53 gene (p53) and the CCR-5 gene (CCR-5):

SEQ ID NO. 1:
(mtDNA1-L16026):
5'-GAT TCT AAT TTA AAC TAT TCT CTG TTC-3';
SEQ ID NO. 2:
(mtDNA2-H16498):
5'-TTA TGA CCC TGA AGT AGG AAC CAG ATG-3';
SEQ ID NO. 3:
(p53-1/exon-7):5'-GGA GGC ACT TGC CAC CCT GCA CAC TGG-3';
SEQ ID NO. 4:
(53-2/intron-8):5'-CTC CTC CAC CGC TTC TTG TTC TGC TTG-3'
SEQ ID NO. 5:
(CCR5-1):5'-GGC TGG TCC TGC CGC TGC TTG TCA T-3';
SEQ ID NO. 6:
(CCR5-2):5'-CTG CTC CCC AGT GGA TCG GGT GTA AAC-3'.

The numbering of the mtDNA primers refers to the 3' end according to Anderson et al. ((1981) Nature 290, 457–465) and L and H refer to the L strand and the H strand respectively. The DEXAS reaction was carried either using ThermoSequenase™ (Tabor, S. and Richardson, C. C. (1995) Proc, Natl. Acad. Sci. USA 92, 6339–6343) (Amersham, UK) reagents or using the following 10×buffer: 500 mM Tris-HCl (pH 9.2), 160 mM (NH$_4$)$_2$SO$_4$, 35 mM MgCl$_2$ (ScienTech Corp., St. Louis, Mo.). Three different nucleotide mixtures were evaluated for the termination: (i) 1:333, 1 mM dATP, 1 mM dCTP, 1 mM dGTP, 1 mM dTTP, in which the A, C, G and T reaction each contained 3 µM of the corresponding dideoxy-nucleotide. (ii) 1:666 also containing in each case 1 mM of each deoxynucleotide but 1.5 µM of the corresponding dideoxynucleotide. (iii) 1:1000 also containing in each case 1 mM of each deoxynucleotide but 1.0 µM of the corresponding dideoxynucleotide. All termination mixtures were prepared using 50 mM Tris-HCl (pH 9.2), 16 mM (NH$_4$)$_2$SO$_4$, 5 mM MgCl$_2$.

A premix of 1 µl (units not defined) Taquenase™ (ScienTech Corp., St. Louis, Mo.) and 1 unit thermostable pyrophosphatase (NEB, Beverly, Mass.) was prepared for each sequencing reaction. In the case of the ThermoSequenase reactions, the reactions were prepared as recommended by the manufacturer. In the other cases a 20 µl mixture of primer (2 pmol to 12 pmol), DNA (15 ng to 1.5 µg), sequencing buffer (2 µl of the 10×buffer, see above) and enzyme was prepared and a 5 µl aliquot of this was added to 2 µl termination mix. The sequencing reactions were carried out in a thermocycler with a heatable cover (MJ-Research, Watertown, Mass.). The reactions were stopped by adding 5 µl formamide (20 mM EDTA (pH 7.4) and 6 mg/ml dextran blue) which was followed by a 4 minute denaturation at 95° C.

The sequencing reactions were analysed on an A.L.F. when FITC-labelled primers were used and on an A.L.F. express when Cy5-labelled primers were used (both Pharmacia Biotech, Uppsala, Sweden). HydroLink Long

EXAMPLE 2
DEXAS of Mitochondrial DNA Sequences

Two oligonucleotides were synthesized both having a length of 27 nucleotides which span a 521 base pair region of the human mitochondrial control region. 27-mers were used to minimize an unspecific annealing of the primers to incorrect priming positions and to enable the reaction temperatures to remain above 62° C. during all synthesis steps. One of the two oligonucleotides was labelled at the 5' end with fluorescein (mtDNA1) whereas the other (mtDNA2) was unlabelled. 4 pmol of each of the primers was mixed with ThermoSequenase™ (Amersham, UK) reagent which contained enzyme (DNA polymerase and thermostable pyrophosphatase), reaction buffer and a mixture of deoxynucleotides and dideoxynucleotide. Different amounts of human DNA (500 ng, 250 ng, 125 ng, 62 ng, 0 ng) were added to individual aliquots of this mixture. 500 ng template DNA but no unlabelled primer was added to one tube. The reactions were incubated for 3 minutes at 95° C. in order to enable a complete denaturation of the template DNA. Subsequently 35 cycles each of 30 sec. at 62° C. and 40 sec. at 95° C. were carried out. The reactions were stopped and denatured by the addition of formamide and heating to 95° C. for 4 min before they were loaded onto an A.L.F. sequencing gel. In the case were no DNA had been added no sequence was detectable. No sequence was detectable when only the labelled primer and no unlabelled primer had been added. However, sequence curves were obtained in cases in which 62 ng or more template had been used. In the reactions in which 250 ng and 500 ng had been used the A.L.F. software was able to determine more than 400 bases.

Using a constant amount of template DNA of 500 ng and a total amount of 12 pmol of the two primers, the ratios between the labelled primer and the unlabelled primer were varied in each case between 3:1, 2:1, 1:1, 1:2 and 1:3. The reaction in which the primers were present in equimolar amounts yielded poor signals whereas all other ratios, independently of whether the labelled or the unlabelled primer was present in excess, yielded better results. The ratios 2:1 and 1:2 yielded the best results. It was surprising and unexpected that both non-equimolar ratios are advantageous. Using 8 pmol of the primer mtDNA1 and 4 pmol of the primer mtDNA2 we presently routinely determine 450 base pairs of the mitochondrial control region.

The ratio of the deoxynucleotides (dNTPs) to dideoxynucleotides (ddNTPs) can be varied in the DEXAS reaction. A higher proportion of dNTPs will probably allow an increased template production in each cycle whereas a higher proportion of ddNTPs would lead to an increased termination of the extension products before the priming position of the second unlabelled primer is reached. The latter products will contribute to the sequence reaction but not to the further template amplification. In order to determine to what extent the ratio of ddNTPs to dNTPs influences the reaction, ddNTPs were mixed with dNTPs in ratios of 1:333, 1:666 and 1:1000 and used in a DEXAS reaction containing 8 pmol of an FITC-labelled primer (mtDNA1), 4 pmol of an unlabelled primer (mtDNA2) and 300 ng human DNA. The reaction conditions were as described above. The results showed that the ratio 1:666 (ddNTPs:dNTPs) yielded stronger signals.

EXAMPLE 3
DEXAS of Single Copies of Human DNA Sequences

Figure 3A:
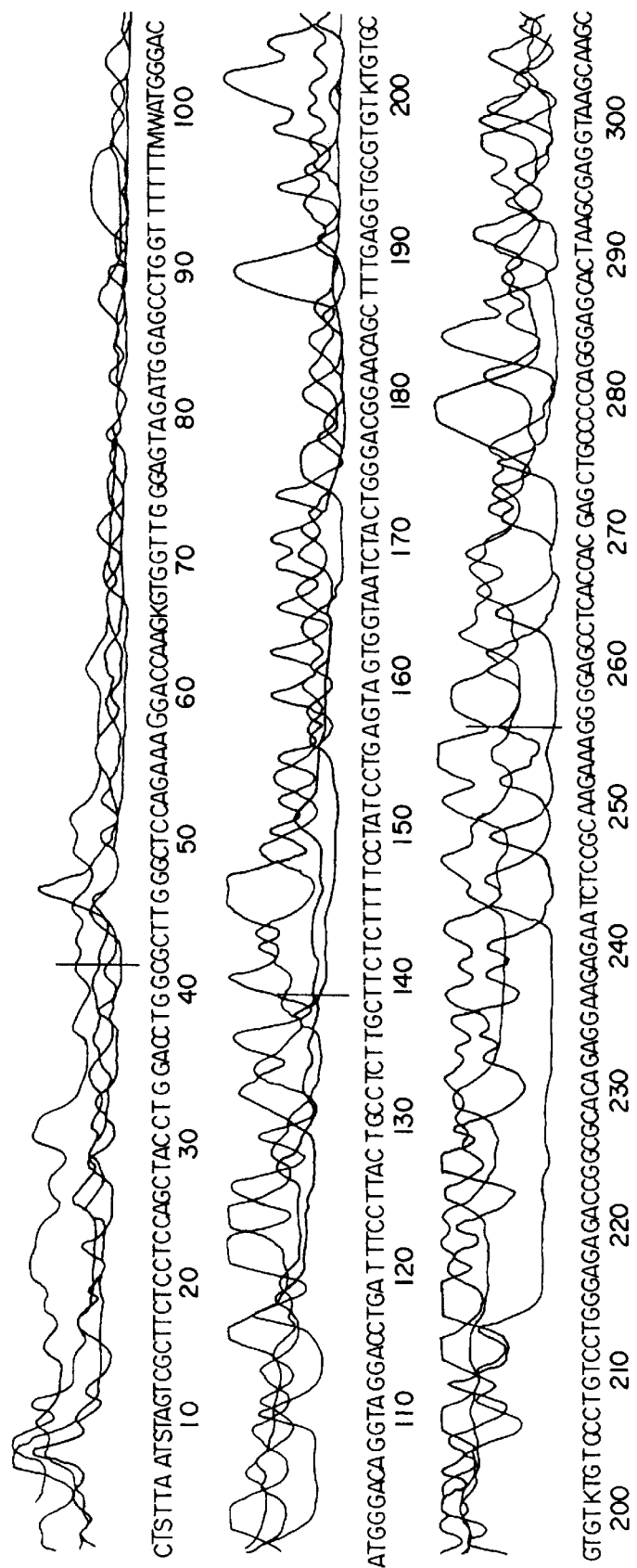
FIGS. 3A and 3B. DEXAS reaction carried out on single-copy genes.

In order to evaluate the applicability of DEXAS to single-copy DNA sequences, primers were synthesized which flank a 507 base pair segment of the intron 7 and the exon 8 of the human p53 gene. DEXAS reactions were prepared which each contained 8 pmol of an FITC-labelled sequencing primer (p53-1), 4 pmol of an unlabelled (p53-2) primers and 3.5 µg, 1.75 µg, 875 ng and 430 ng human DNA. These reactions were denatured for 3 minutes at 95° C. and 40 cycles comprising 30 seconds at 62° C. and 40 seconds at 95° C. were carried out. The results showed a clearly readable sequence. In order to improve the results various modifications of the protocol were evaluated. The annealing temperature was increased and the amount of the sequencing primer was reduced. Additionally the number of cycles was increased to 47 and various primer ratios and template concentrations were evaluated. The best results were obtained using 8 pmol of the FITC-labelled primer and 4 pmol of the unlabelled primer and cycling temperatures of 30 seconds at 68° C. and 30 seconds at 95° C. These conditions yielded between 260 and 320 bases of the sequence with 1 to 5 ambiguities per reaction in five experiments (FIG. 3A). If about 1 µg or more template was used, the sequence signals were read with the A.L.F. software using automated processing.

Figure 3B:
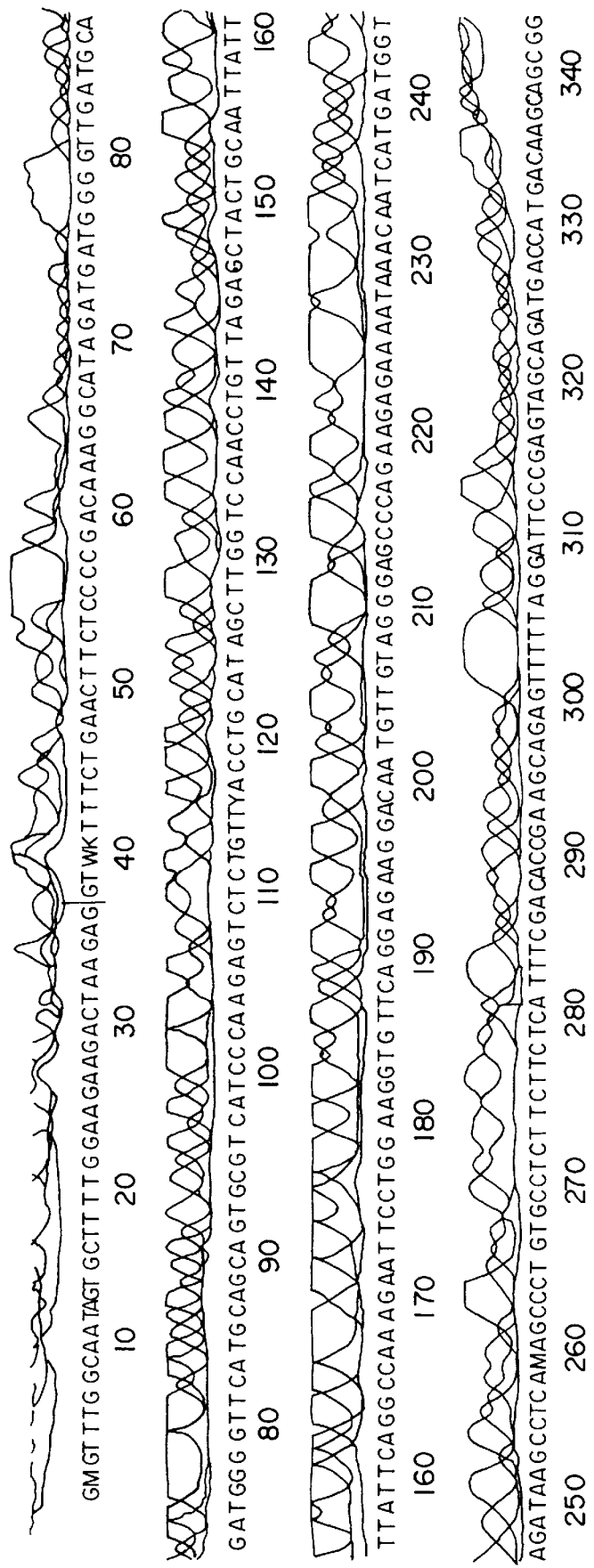

In order to further evaluate the general applicability of DEXAS to single copy genes, primers were synthesized which flank a 382 base pair segment of the CCR-5 gene. 3 pmol of the CCR5-1, 6 pmol of the FITC-labelled primer CCR5-2, 0.5–1.0 µg template DNA and 45 cycles DEXAS were used. In the sequence reactions carried out on 40 samples the reading lengths varied between 230 bp and 351 bp (average 294 bp). A typical reaction is shown in FIG. 3B.

EXAMPLE 4
Simultaneous Sequencing of Both DNA Strands

Figure 4:
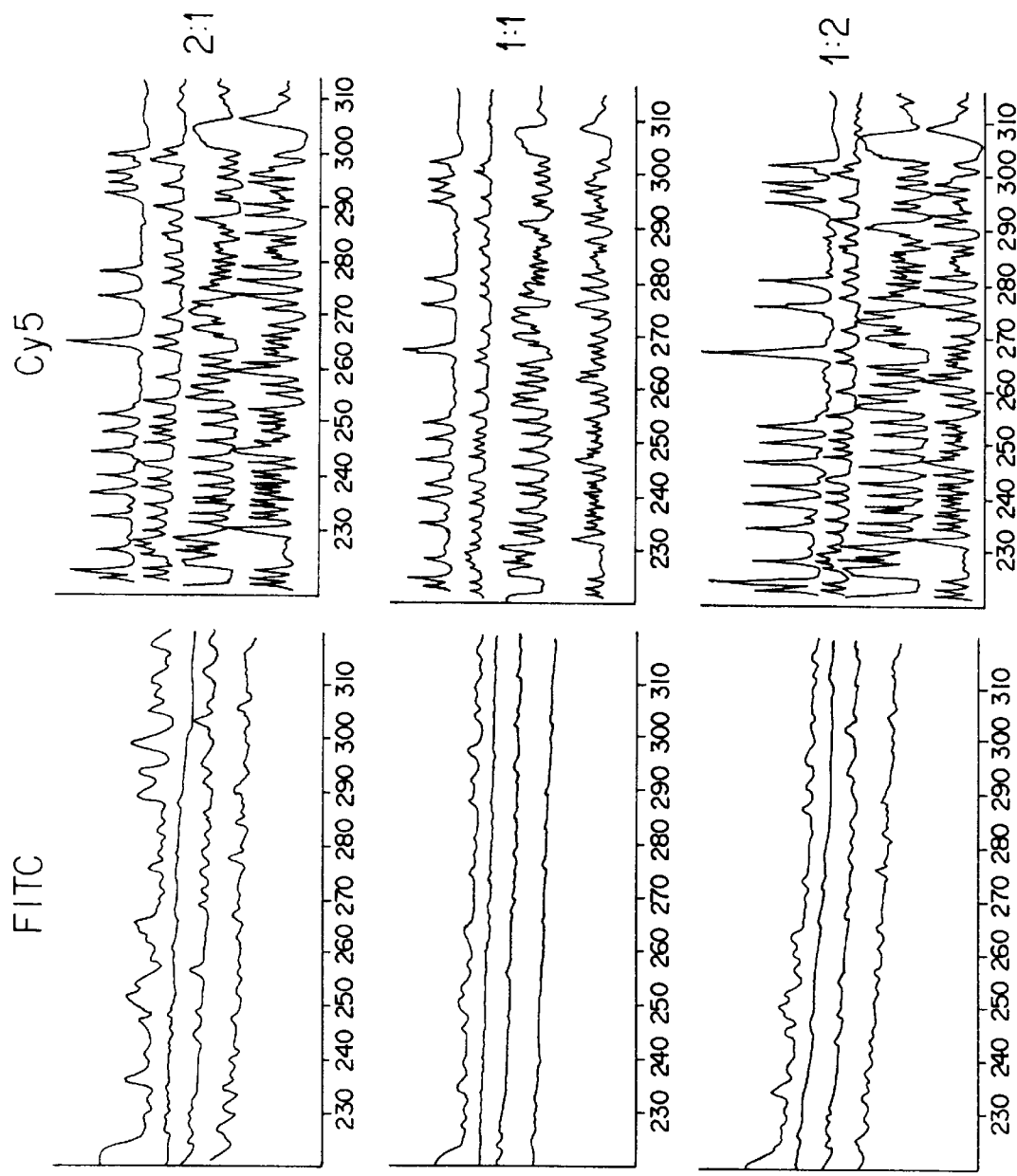
FIG. 4. Two colour DEXAS reaction using different oligonucleotide ratios. Each of the reactions was carried out using 250 ng genomic human DNA and a total amount of 12 pmol primer. MtDNA1 was labelled with FITC (left panel) and MtDNA2 was labelled with Cy5 (right panel). The ratios between FITC-MtDNA1 and Cy5-MtDNA2 were varied between 2:1 (upper panel), 1:1 (middle panel) and 1:2 (lower panel). The largest signal-to-noise ratio for both primers is achieved when a ratio of 2:1 is used. The raw data of the A.L.F. and of the A.L.F. express instruments are shown. The assignment of the base signals from top to bottom is C, A, G, and T respectively.
Figure 5:
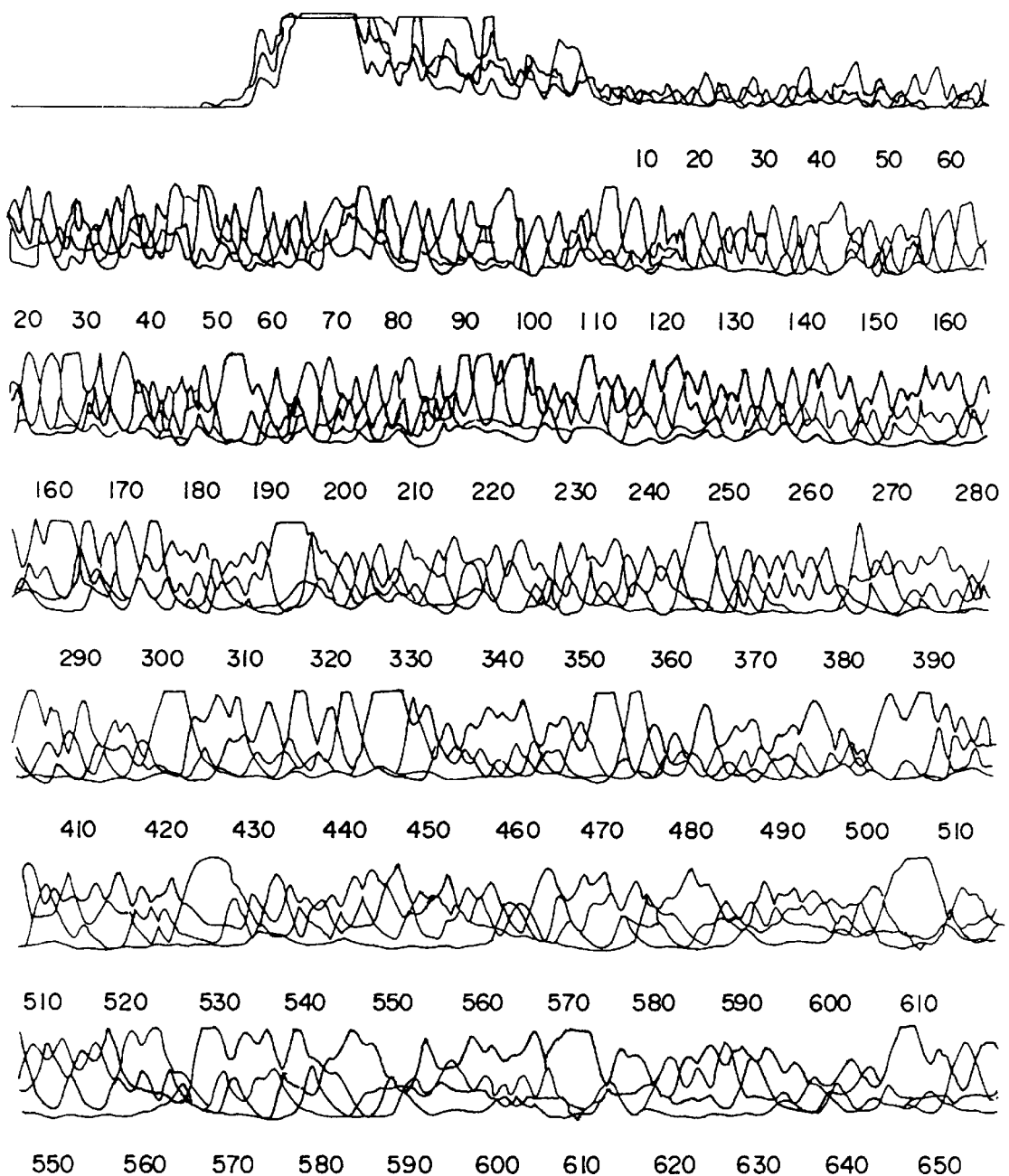
FIG. 5. DEXAS was carried out using simultaneously a fluorescein-labelled 'T3' primer and a Cy5-labelled 'universal' primer. The figure shows the sequence traces obtained with the Cy5-labelled primer. A sequence was obtained from the sequence traces, though the sequence is not shown in FIG. 5. The two primers were used in a single reaction using one bacterial colony. 4 µl of each was analysed on an A.L.F. or an A.L.F. express. The reaction with the 'T3' primer yielded 407 bases and the reaction with the 'universal' primer yielded 668 bases.

It was shown that it is possible to sequence both complementary DNA strands of plasmid DNA in a single reaction using two different fluorescently-labelled primers (Wiemann, S., et al., (1995) *Analytical Biochemistry* 224, 117–121). The applicability of this approach to DEXAS was analysed using an FITC-labelled primer (mtDNA1), a Cy5-labelled primer (mtDNA2) and 500 ng human DNA as the template. While retaining the above reaction conditions the primer ratios were varied (FITC-mtDNA1:Cy5-mtDNA2) (3:1, 2:1, 1:1, 1:2 and 1:3). After the cycling reaction and denaturation 5 µl of the reaction was applied to an A.L.F. or an A.L.F. express instrument. As in previous experiments considerably poorer results were obtained if equimolar amounts of primer were used compared to reactions in which non-equimolar amounts were used (FIG. 4). A ratio of 2:1 at a total amount of 12 pmol gave the best signal-to-noise ratio. In such reactions 450 bases were read on both strands without yielding ambiguous positions. The observation that a larger amount of FITC-labelled primer than Cy5-labelled primer is advantageous is probably due to experiments it was possible to show that the two colour approach can also be applied to single-copy the better signal-to-noise ratio of Cy5 compared to FITC. In further genes.

What is claimed is:

1. A method for sequencing at least a portion of a DNA molecule involving simultaneously amplifying the DNA molecule and generating full-length and truncated copies of said DNA molecule for sequencing, comprising the steps of
    (a) subjecting a mixture A in a single step to DNA amplification and generation of full-length and truncated copies by subjecting the mixture A to a thermocycling reaction, wherein the thermocycling reaction comprises heat denaturation, annealing and synthesis, wherein said mixture A comprises
        said DNA molecule,
        a first primer which is able to hybridize with a strand of said DNA molecule,
        a second primer which is able to hybridize with a strand of DNA complementary to the strand with which the first primer is able to hybridize, wherein at least one of the first and second primers is labelled,
        a reaction buffer,
        deoxynucleotides or deoxynucleotide derivatives, wherein said deoxynucleotide derivatives are able to be incorporated by a thermostable DNA polymerase into growing DNA molecules in place of one of dATP, dGTP, dTTP or dCTP,
        at least one dideoxynucleotide or another terminating nucleotide,
        a thermostable DNA polymerase having a reduced, compared to wild-type Taq DNA polymerase, discrimination against the incorporation of dideoxynucleotides relative to deoxynucleotides, and
        at least one polymerase-inhibiting antibody against said thermostable DNA polymerase, which polymerase-inhibiting antibody loses inhibitory ability, thereby allowing said thermostable DNA polymerase to be active, at a temperature which is at least the temperature at which unspecifically hybridized primers separate from a DNA molecule,
    to simultaneously make full-length and truncated copies of said DNA molecule, wherein the full-length copies have a length equal to that of at least a portion of said DNA molecule spanning the binding sites of the first and second primers;
    (b) generating a sequence ladder by separating at least the truncated copies of said DNA molecule; and thereafter
    (c) reading the sequence ladder to obtain the sequence of said at least a portion of said DNA molecule.

2. The method of claim 1, wherein the deoxynucleotide derivatives are thionucleotides, 7-deaza-2'-dGTP, 7-deaza-2'-dATP or deoxyinosine triphosphate.

3. The method of claim 1, wherein said another terminating nucleotide is 3'-aminonucleotide or a nucleotide having an ester group at the 3' position.

4. The method of claim 1, wherein said thermostable DNA polymerase is a Taq DNA polymerase lacking 5'-3' exonuclease activity and having a Tabor-Richardson mutation or a functional derivative thereof.

5. The method of claim 4, wherein said thermostable DNA polymerase is AMPLITAQFS, TAQUENASE, THEROSEQUENASE or functional derivatives thereof.

6. The method of claim 5, wherein said thermostable DNA polymerase is THERMOSEQUENASE or a functional derivative thereof.

7. The method of claim 1, wherein the thermocycling reaction in step (a) is carried out without interruption in a single container, vessel or tube.

8. The method of claim 1, wherein the initial molar ratio of said first primer to said second primer is not equal to 1:1 in step (a).

9. The method of claim 8, wherein the initial molar ratio of said first primer to said second primer is about 2:1 to about 3:1 in step (a).

10. The method of claim 9, wherein the initial molar ratio of said first primer to said second primer is 2:1 in step (a).

11. The method of claim 1, wherein the first and second primers are differently labelled.

12. The method of claim 1, wherein the first and second primers independently have a length of at least 25 nucleotides.

13. The method of claim 1, wherein the initial ratio of said deoxynucleotides and deoxynucleotide derivatives to said dideoxynucleotide and another terminating nucleotide is between 100:1 and 1000:1.

14. The method of claim 13, wherein the initial ratio of said deoxynucleotides and deoxynucleotide derivatives to said dideoxynucleotide and another terminating nucleotide is between 300:1 and 600:1.

15. The method of claim 1, wherein the initial concentration of said deoxynucleotides or deoxynucleotide derivatives in mixture A are between about 300 $\mu$M and 2 mM.

16. The method of claim 1, wherein the initial concentration of said dideoxynucleotide or another terminating nucleotide in mixture A is between about 1 and 5 $\mu$M.

17. The method of claim 1, wherein mixture A further comprises at least one thermostable pyrophosphatase.

18. The method of claim 1, wherein the annealing and synthesis of the thermocycling reaction are carried out at a temperature of at least about 66° C.

19. The method of claim 18, wherein the annealing and synthesis of the thermocycling reaction are carried out at a temperature of at least about 68° C.

20. The method of claim 1, wherein said DNA molecule in mixture A is obtained from a body fluid, hairs, an individual cell, cells or fractions thereof, a tissue or fractions thereof, a cell culture or fractions thereof, a tissue culture or fractions thereof, or bacteriophages.

21. The method of claim 1, wherein said DNA molecule is in a complex mixture of nucleic acids.

22. The method of claim 1, wherein said DNA molecule is a single-copy DNA.

23. The method of claim 1, wherein said DNA molecule in mixture A is mitochondrial DNA.

24. The method of claim 1, wherein said DNA molecule in mixture A is unpurified plasmid DNA from bacteria.

25. The method of claim 1, wherein said DNA molecule in mixture A is unpurified single-stranded or double-stranded DNA from bacteriophages.

26. The method of claim 21, wherein said complex mixture of nucleic acids in mixture A is total genomic DNA.

27. The method of claim 26, wherein said total genomic DNA is unpurified.

28. A kit for sequencing at least a portion of a nucleic acid molecule comprising
    deoxynucleotides or deoxynucleotide derivatives, which deoxynucleotide derivatives are able to be incorporated by a thermostable DNA polymerase into growing DNA molecules in place of one of dATP, dGTP, dTTP or dCTP;
    at least one dideoxynucleotide or another terminating nucleotide;
    a thermostable DNA polymerase having a reduced, compared with wild-type Taq polymerase, discrimination against the incorporation of dideoxynucleotides relative to deoxynucleotides; and
    at least one polymerase-inhibiting antibody against said thermostable DNA polymerase, which polymerase-inhibiting antibody loses inhibitory ability, thereby allowing said thermostable DNA polymerase to be active, at a temperature which is at least the temperature unspecifically hybridized primers separate from a DNA molecule.

29. The kit of claim 28, wherein said deoxynucleotide derivatives are thionucleotides, 7-deaza-2'-dGTP, 7-deaza-2'-dATP or deoxyinosine triphosphate.

30. The kit of claim 28, wherein said another terminating nucleotide is a 3'-aminonucleotide or a nucleotide having an ester group at the 3' position.

31. The kit of claim 28, wherein said thermostable DNA polymerase is a Taq DNA polymerase lacking 5'-3' exonuclease activity and having a Tabor-Richardson mutation or a functional derivative thereof.

32. The kit of claim 28, wherein said thermostable DNA polymerase is AMPLITAQFS, TAQUENASE, THERMOSEQUENASE or functional derivatives thereof.

33. The kit of claim 32, wherein said thermostable DNA polymerase is THERMOSEQUENASE or functional derivatives thereof.

34. The kit of claim 28, further comprising at least one thermostable pyrophosphatase.

35. The kit of claim 28, wherein the molar ratio of said deoxynucleotides and deoxynucleotide derivatives to said dideoxynucleotide and another terminating nucleotide is between 100:1 and 1000:1.

36. The kit of claim 35, wherein the molar ratio of said deoxynucleotides and deoxynucleotide derivatives to said dideoxynucleotide and another terminating nucleotide is between 300:1 and 600:1.

37. The kit of claim 28, further comprising first and second primers, wherein (1) said first primer is able to hybridize with a strand of DNA molecule to be sequenced, and (2) said second primer is able to hybridize with a strand of said DNA molecule complementary to the strand said first primer is able to hybridize with, wherein at least one of the first and second primers is labelled.

38. The kit of claim 37, wherein the molar ratio of said first primer to said second primer is different from 1:1.

39. The kit of claim 38, wherein the molar ratio of said first primer to said second primer is about 2:1 to about 3:1.

40. The kit of claim 39, wherein the molar ratio of said first primer to said second primer is 2:1.

41. The kit of claim 37, wherein the first and second primers are differently labelled.

42. The kit of claim 37, wherein the first and second primers independently have a length of at least 25 nucleotides.

* * * * *